(12) United States Patent
Buerk et al.

(10) Patent No.: US 9,888,834 B2
(45) Date of Patent: Feb. 13, 2018

(54) ENDOSCOPE WITH A WINDOW AND PROCESS TO MANUFACTURE AN ENDOSCOPE

(75) Inventors: Andre Buerk, Villingen-Schwenningen (DE); Stefan Heseler, Trossingen (DE); Elmar Teichtmann, Eppingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 875 days.

(21) Appl. No.: 12/817,615

(22) Filed: Jun. 17, 2010

(65) Prior Publication Data

US 2010/0324372 A1    Dec. 23, 2010

(30) Foreign Application Priority Data

Jun. 17, 2009   (DE) .................. 10 2009 025 660

(51) Int. Cl.
*A61B 1/00* (2006.01)
*A61B 1/04* (2006.01)
*A61B 1/06* (2006.01)
*G02B 23/24* (2006.01)

(52) U.S. Cl.
CPC ........ *A61B 1/00096* (2013.01); *A61B 1/0011* (2013.01); *G02B 23/2423* (2013.01); *Y10T 29/49826* (2015.01)

(58) Field of Classification Search
CPC . A61B 1/00096; A61B 1/00142; A61B 1/002; A61B 1/0008; A61B 1/055
See application file for complete search history.

(56) References Cited

U.S. PATENT DOCUMENTS

| | | | | |
|---|---|---|---|---|
| 4,779,613 A * | 10/1988 | Hashiguchi et al. | ......... | 600/169 |
| 5,536,244 A | 7/1996 | Müller et al. | | |
| 5,599,278 A * | 2/1997 | Hibbard | ........................ | 600/133 |
| 6,100,972 A * | 8/2000 | Harley et al. | .............. | 356/241.1 |
| 6,110,105 A | 8/2000 | Durell | | |
| 6,478,730 B1 * | 11/2002 | Bala et al. | ..................... | 600/121 |
| 6,572,536 B1 * | 6/2003 | Bon et al. | ..................... | 600/133 |
| 6,638,216 B1 | 10/2003 | Durell | | |
| RE43,281 E * | 3/2012 | Higuma et al. | ............... | 600/133 |
| 2004/0176662 A1 * | 9/2004 | Forkey et al. | ................ | 600/133 |
| 2004/0236183 A1 * | 11/2004 | Durell | ........................... | 600/173 |
| 2008/0228035 A1 * | 9/2008 | Hagihara et al. | ............. | 600/121 |
| 2009/0131931 A1 * | 5/2009 | Lee et al. | ........................ | 606/41 |

FOREIGN PATENT DOCUMENTS

| | | |
|---|---|---|
| DE | 3740417 A1 | 6/1989 |
| DE | 9309545 U1 | 8/1993 |
| DE | 10205735 A1 | 8/2003 |
| WO | 0122865 A1 | 4/2001 |

OTHER PUBLICATIONS

Material Expansion Coefficients, Laser and Optics User's Manual. 2002 Agilent Technologies. pp. 6 and 8.*

* cited by examiner

*Primary Examiner* — Alexandra L Newton
(74) *Attorney, Agent, or Firm* — Whitmyer IP Group LLC

(57) ABSTRACT

An endoscope includes a window on a distal end of the endoscope, an interior body with a first material on the distal end, and a mantle with a second material on the distal end, such that the window and the interior body are joined.

11 Claims, 3 Drawing Sheets

ENDOSCOPE WITH A WINDOW AND PROCESS TO MANUFACTURE AN ENDOSCOPE

CROSS-REFERENCE TO RELATED APPLICATIONS

The present application claims priority of German patent application No. 10 2009 02.1 filed on Jun. 17, 2009.

FIELD OF THE INVENTION

The present invention relates to an endoscope having a window on the distal end and a process to manufacture an endoscope. In particular, the present invention relates to an endoscope in which an angle between the line of vision and the axial direction of the endoscope can be varied, for instance by means of a pivotable prism or mirror.

BACKGROUND OF THE INVENTION

Minimally invasive surgical procedures have numerous advantages, such as a reduced traumatization and a more rapid recovery on the part of the patient, reduced demands on anesthesia, briefer patient stays in the operating room, and subsequently lower costs in the clinic as well as in general. An endoscope used in minimally invasive surgery must fulfill numerous requirements simultaneously. In particular, it must include strong reliability and/or availability and a long useful lifetime, despite the thermal impact from autoclaving following each use.

Variable view endoscopes are already described in the art in U.S. Pat. No. 6,110,105 A, U.S. Pat. No. 6,638,216 B1, US 2004/0236183 A1, and WO 01/22865 A1. Variable view endoscopes for technical, non-medical applications (also called boroscopes) are already commercially available. Endoscopes for medical applications with a line of vision that can vary over a wide angle are not yet available, however. The reason, among other factors, is found in the interface between the mantle or housing of the endoscope and the transparent window, which must be curved to achieve a wide angle. This interface must also remain hermetically insulated even after many cycles of preparation, particularly autoclaving, in order to prevent penetration of moisture into the interior of the endoscope and the damaging of the lens by moisture penetration.

In particular, the applicant has been obliged to observe that in other types of endoscopes with plane, circular, or elliptical windows, proven joining techniques for durable mechanical connection of the window with the housing or mantle of the endoscope with curved windows cannot be applied. Because of the curvature, the comparatively great total surface, and a clearly non-elliptical contour, the temperatures and temperature changes and resulting variable length-wise extension with conventional material pairings in a joining process as well as in a customary autoclaving process require mechanical tensions that, after a brief time, lead to fissures or fractures in the window or in the joining seam. Investigations have shown that even with a geometric modification of components made of customary materials, significant tensions arise in the joining process that can result in fissures or fractures of the window, even when this process is withstood without damage, at the latest during preparation.

One object of the present invention consists in creating an improved endoscope and an improved process to manufacture an endoscope with a window, in particular a curved window.

SUMMARY OF THE INVENTION

This object is achieved through the objects of the independent claims.

Refinements are indicated in the dependent claims.

Various embodiments of the present invention are based on the idea of dividing the tasks of the joining seam on the edge of a window into a first insulating seam between the window and mantle or housing of the endoscope and a second, hermetically insulated seam, which reliably prevents the penetration of moisture, even under the conditions of autoclaving, into an area in which the optical components of the endoscope are located. In other words, the window is joined to an interior body made of an especially suited material—especially in view of the thermal expansion coefficient. In this manner the window can close off an opening to a hollow space in the interior body in a manner that is still reliably hermetically insulated even after numerous autoclaving cycles. The material of the interior body can largely be freely selected, because it can avoid forming any external surface of the endoscope but rather can be enclosed by a mantle or housing. Only the material of the mantle or housing is required to fulfill the customary requirements of an endoscope, in particular biocompatibility. With a comparatively simple insulation between the edge of the window and the edge of a corresponding opening in the mantle or housing, it is possible to ensure that the human or animal body in which the endoscope is to be used does not come into contact with the material of the interior body.

An endoscope includes a window at a distal end of the endoscope, an interior body with a first material on the distal end, and a mantle with a second material on the distal end, such that the window and the interior body are joined.

The interior body, which can also be called the inner segment, in particular forms no external surface of the endoscope, so that only the mantle or housing of the endoscope must be biocompatible. The first material, which is included in the interior body at least on the distal end, can then be selected in such a way that in particular its extension at elevated temperatures, as occur upon joining the window and interior body or upon autoclaving, can be adjusted to that of the window. In particular, the difference in thermal expansion coefficients of the first material and of a material of the window (for instance, sapphire or another corundum) can be smaller than a difference in the thermal expansion coefficients of the second material and of the material of the window.

For example, non-stainless steel 1.4301 or 1.4305 at temperatures starting at 20 degrees C. has a linear thermal expansion coefficient of approximately $16 \times 10^{-6}$ $K^{-1}$. Sapphire is particularly suited as a material for the window because of its extreme hardness, but it has a linear heat expansion coefficient of only about $6 \times 10^{-6}$ $K^{-1}$. It is therefore advantageous to select a first material with a thermal expansion coefficient whose difference from the thermal expansion coefficient of the material of the window, rather than approximately $10 \times 10^{-6}$ $K^{-1}$, is only $5 \times 10^{-6}$ $K^{-1}$ or better only $2 \times 10^{-6}$ $K^{-1}$ or even better $1 \times 10^{-6}$ $K^{-1}$ or less. In using a window of sapphire, therefore, a first material with a linear heat expansion coefficient of at most $8 \times 10^{-6}$ $K^{-1}$ is especially appropriate, but even more suitable are materials with a linear heat expansion coefficient of at most $7 \times 10^{-6}$ $K^{-1}$ or with a heat expansion coefficient between $5.5\times10^{-6}$ $K^{-1}$ and $6.0\times10^{-6}$ $K^{-1}$ or $6.5\times10^{-6}$ $K^{-1}$. These requirements are met, for instance, by NiFe alloys with a nickel portion of about 42% by weight or NiCoFe alloys with a nickel portion of about 29% by weight and a cobalt portion of about 17% by weight. Materials of this type are also referred to as melting materials or expansion materials and are marketed, for instance, by the Deutsche Nickel GmbH company under the brand name Dilaton and designated as "29/18," "42," and "42 LC. In addition, however, other melting alloys can be used.

The endoscope is in particular a variable view endoscope or an endoscope with a variable angle between the line of vision and the axial direction of the endoscope. To vary the angle between line of vision and axial direction, the endoscope comprises, for instance, a pivotable prism, a pivotable mirror, or a pivotable video camera near the window. In particular for an endoscope of this type, the window can be curved in at least one direction. The window can hermetically close an opening to a hollow space in the interior body. In particular for a hermetic lock for an opening to a hollow space in the interior of the body, the window and the interior body can be soldered together. It is possible to use both hard and soft soldering methods, in particular in conjunction with a gold solder. A cementing seam and/or an insulation or another flexible material can be provided between the border of the window and the mantle. To further reduce the risk of breakage of the window by thermally caused mechanical tensions, the window can have rounded corners.

The mantle can include a terminal portion on the distal end and a shaft portion, such that the terminal portion and the shaft portion are joined. The shaft portion, in particular, is essentially tubular in shape. The terminal portion includes in particular an opening that corresponds to the window or to its contour. The terminal portion is configured, for instance, to be suspended on an overlapping section on a distal end of the interior body and by pivoting can be moved into its foreseen position around an axis close to the overlapping section. Alternatively, the terminal portion is configured, for instance, to be moved to the distal end of the endoscope in a bent or straight linear motion, which can be combined with a rotation and at least in its final portion runs non-parallel to the axis of the endoscope. In this manner the closing unit can simultaneously be moved to the shaft portion, with which it is then joined. Through one of the aforementioned configurations of the mantle, the interior body can be fully enclosed with the exception of the surface of the window, after the window and the interior body are joined.

The endoscope can comprise several light outlet openings on two opposite sides of the window, such that the light outlet openings on one side of the window are arranged to be set off from the light outlet openings on the other side of the window. This makes possible a more uniform illumination of a space examined with the endoscope. A symmetrical arrangement of the light outlet openings is also possible, such as by providing a uniform illumination by other means.

An endoscope includes—independently from, but entirely in combination with, the aforementioned attributes of the window and of an interior body of the endoscope—a mantle with a terminal portion on the distal end and a shaft portion, such that the terminal portion and the shaft portion are joined. The shaft portion in particular is essentially tubular in shape. The terminal portion includes in particular an opening that corresponds to the window or to its contour. The terminal portion is configured, for instance, to be suspended on an overlapping section on a distal end of the interior body and can be moved into its foreseen position by pivoting around an axis close to the overlapping section. Alternatively, the terminal portion, for instance, is configured so that it can be moved to the distal end of the endoscope in a curved or straight linear motion, which can be combined with a rotation and at least in its last portion runs non-parallel to the axis of the endoscope. In this manner the terminal portion can simultaneously be moved to the shaft portion, with which it is then joined. As a result of one of the aforementioned configurations of the mantle, the interior body can be fully enclosed with the exception of the surface of the window, after the window and the interior body are joined.

In a process to manufacture an endoscope, a window is joined to a distal end of an interior body, a mantle is positioned around the instrument body, and a joint is insulated between the window and the mantle of the endoscope. Before or after insulating the joint, a connecting portion, which surrounds the window, and a shaft portion of the mantle can be joined. After joining the window to the distal end of the interior body and before insulating the joint, the terminal portion can be suspended on an overlapping section on a distal end of the interior body and can be pivoted around an axis close to the overlapping section. With the aforementioned process, one of the endoscopes described above, in particular, can be produced.

In an additional process to manufacture an endoscope, a terminal portion, which surrounds a window, and a shaft portion can be joined to a mantle, which in particular forms the entire surface of the distal end of the endoscope, apart from the window. Before joining, the terminal portion can be moved to the distal end of the endoscope in a straight-line or non-straight-line motion, but in any case one that is not parallel to the axis of the endoscope. This motion can be superimposed or supplemented by a rotation motion. Alternatively, the terminal portion is suspended first, for instance on the distal end of the endoscope and then with a pivoting motion is brought into its final position relative to the other parts of the endoscope.

BRIEF DESCRIPTION OF THE DRAWINGS

Hereafter, embodiments are described in greater detail with reference to the appended illustrations.

DETAILED DESCRIPTION OF THE INVENTION

Figure 1:
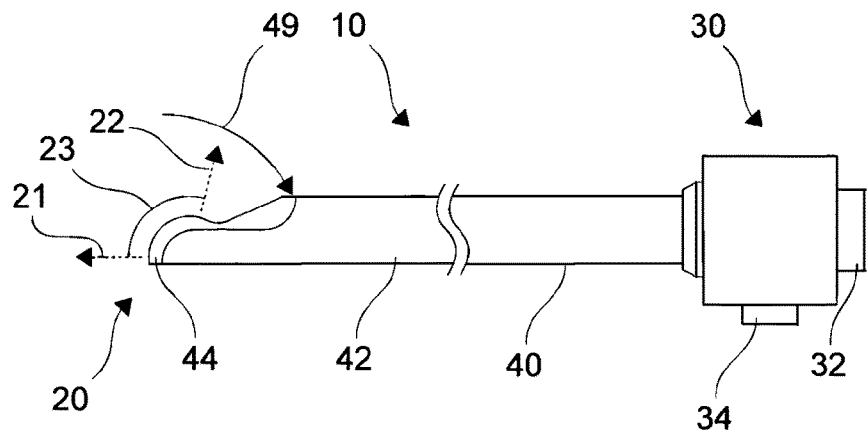
FIG. 1 is a schematic depiction of an endoscope.

FIG. 1 shows a schematic view of an endoscope 10 in a side view. A longitudinal axis of the endoscope 10, along which the endoscope 10 is extended for a great distance, lies parallel to the plane of projection. The length of the endoscope 10 between a distal end 20 and a proximal end 30 is shown markedly abbreviated.

The endoscope 10 is configured for variable lines of vision between a first extreme line of vision 21 and a second extreme line of vision 22, such that the first extreme line of vision 21 is approximately parallel to the axis of the endoscope 10. To vary the line of vision, the endoscope 10 comprises, for instance, a pivotable mirror, a pivotable prism, or a pivotable video camera, such as an electronic image recorder, in the distal end 20. The angle 23 between the extreme lines of vision 21, 22 is preferably greater than 90 degrees, in particular 120 degrees.

The proximal end 30 of the endoscope 10 contains a first coupling 32 and a second coupling 34 for coupling the endoscope 10 with a video camera, a light source, an eyepiece, and/or other devices not shown in FIG. 1.

The endoscope 10 includes a mantle 40, which, as described more closely below, separates the endoscope 10 essentially completely from the outside, except for the proximal end 30, and forms its external surface. The mantle 40 includes an essentially tubular shaft portion 42 and a terminal portion 44 on the distal end 20.

Also shown in FIG. 1 is an arrow 49, whose significance is described later in connection with FIGS. 3 and 5.

Figure 2:
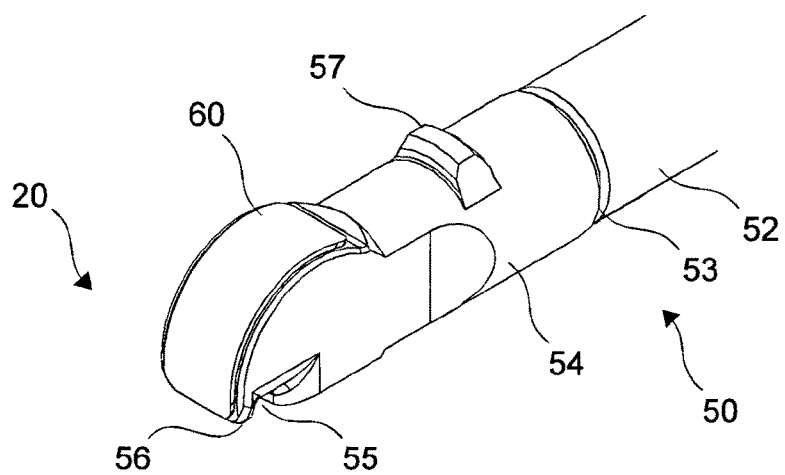
FIG. 2 is a schematic axonometric depiction of an interior body of an endoscope.
Figure 3:
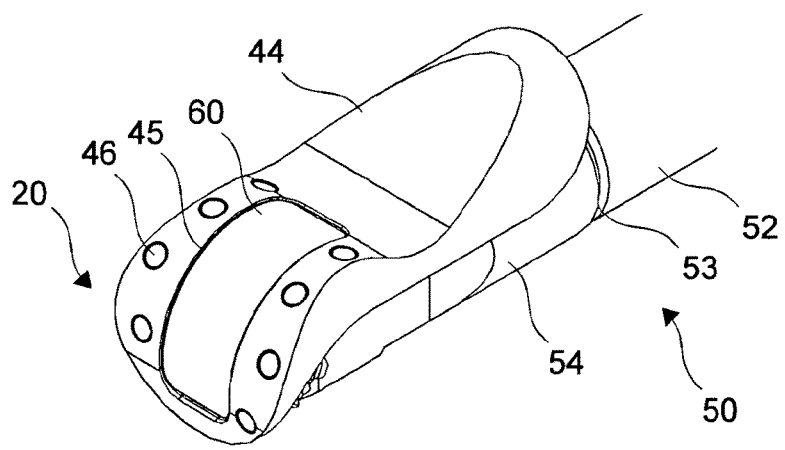
FIG. 3 is a schematic axonometric depiction of a distal end of an endoscope.
Figure 4:
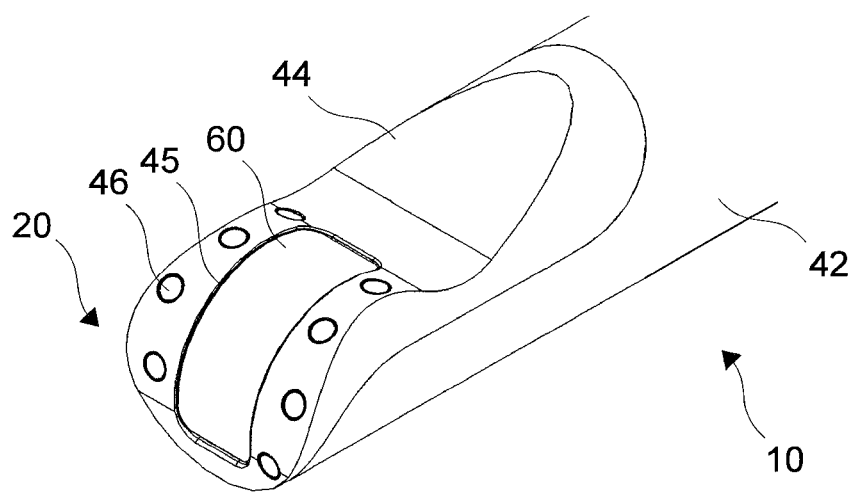
FIG. 4 is a schematic axonometric depiction of a distal end of an endoscope.

FIGS. 2 through 4 present schematically axonometric depictions of the distal end 20 of the endoscope 10 in various stages of its production.

FIG. 2 shows a schematic view of an interior body 50 with a shaft portion 52, which is permanently mechanically connected with an end portion 54 on its joint area 53, for instance by welding or soldering. The shaft portion 52 has, for instance, the shape of a tube with, for instance, circular ring cross-section. The end portion 54 has a more complex shape with a hollow area not visible in FIG. 2. The hollow area in the end portion 54 extends from the distal end 20 to the shaft portion 52, continuing into the shaft portion's lumen. The end portion 54 comprises a groove 55 and a stud 56 directly on the distal end 20. In addition, the end portion 54 comprises a cam 57 on a side at a distance from the groove 55 and stud 56 and close to the shaft portion 52.

In addition, the end portion 54 comprises an opening to the entire hollow area, which opening is closed off by a window 60. The window 60 has, in particular, the shape of a section of a cylindrical hollow body with constant wall thickness. It can also take the form of a section of a hollow body curved in two directions. In both cases the wall thickness can be either constant or variable. The window 60 contains sapphire (in particular, monocrystalline sapphire), another corundum, or another transparent and, in particular, colorless material. The window 60 is joined to the end portion 54 by hard soldering or soft soldering, in particular by means of a gold solder, and hermetically encloses the end portion's opening.

FIG. 3 shows the distal end 20 of the endoscope 10 after the terminal portion 44 of the mantle has been applied. The terminal portion 44 comprises a stud, which cannot be seen because it is hidden in this perspective and which engages in the groove 55, shown in FIG. 2, behind the stud 56 on the end portion 54. To apply the terminal portion 44, this stud is inserted in or applied on the terminal portion 44 before or inside the groove 55, and then the terminal portion 44 is brought into the position shown in FIG. 3 with a pivot motion shown by the arrow 49 in FIG. 1. In the position of the terminal portion 44 shown in FIG. 3, said portion is contiguous with the cam 57. Alternatively, in the position of the terminal portion 44 shown in FIG. 3, the cam 57 engages in a corresponding recess in the terminal portion 44.

The relative position of the terminal portion 44 of the mantle 40 with respect to the end portion 54 of the interior body 50 is defined by the groove 55 and/or the stud 56 and the cam 57 on the end portion 54 of the interior body 50, on the one hand, and, on the other hand, by the aforementioned stud, not visible in FIG. 3, on the terminal portion 44 and, possibly, the likewise aforementioned recess in the terminal portion 44 of the mantle 40. With the terminal portion 44 in this position, the window 60 lies in a corresponding opening 45 of the terminal portion 44.

Between the window 60 or its outer border, on the one hand, and the terminal portion 44 or the border of the opening 45 that corresponds with the window 60, on the other hand, an insulation is applied, for instance in the form of an O-ring made of an elastomer and/or in the form of cement, silicon, resin, or another polymer, which is applied in ductile form in the space between the window 60 and the terminal portion 44 and hardens there.

Several light outlet openings 46 are positioned on both sides of the window 60 situated opposite to one another, parallel to a plane containing the axis of the endoscope 10. The light outlet openings 46 on one side of the window 60 are set off from, possibly symmetrically to, the light outlet openings 46 on the other side of the window 60. The light outlet openings 46 are, for instance, coupled with optical fibers that run along the endoscope 10 from the proximal end 30 to the distal end 20. The opening angles and alignments of the individual light outlet openings are selected in such a way that light emitted from the light outlet openings 46 illuminates as uniformly as possible a hollow space observed by means of the endoscope 10.

FIG. 4 shows the distal end 20 of the endoscope 10 after the shaft portion 42 of the mantel 40 has been slid into place over the interior body 50 in the direction from the proximal end 30 toward the distal end 20. With the shaft portion 42 and terminal portion 44 in the position shown in FIG. 4, their borders are contiguous with one another and can be joined, for instance by soldering. After the joining, the endoscope 20—except for the proximal end 30 and the surface of the window 60—is completely surrounded by the mantle 40 consisting of the shaft portion 42 and the terminal portion 44. In other words, the mantle 40—except for the proximal end 30 and the window 60—forms the entire external surface of the endoscope 10. When the endoscope is applied to a human or animal body, said body comes into contact only with the mantle 40 and the window 60, not with the interior body 50.

Instead of applying the terminal portion 44, as described above with reference to FIGS. 1 and 3, in or to the groove 55 of the end portion 54 by suspending or inserting it, and then pivoting 49 it, the terminal portion 44 can also be placed on the end portion 54 of the interior body 50, for instance, in a linear motion in the plane of projection of FIG. 1 and at an angle of approximately 60 degrees to the longitudinal axis of the endoscope 10.

An alternative possibility for applying the terminal portion 44 is a two-part process in which the terminal portion 44 consists of a first part of the terminal portion 44 and a second part of the terminal portion 44 and the two parts are each pushed up or rotated into place by the corresponding side and then are joined, for instance by welding.

Figure 5:
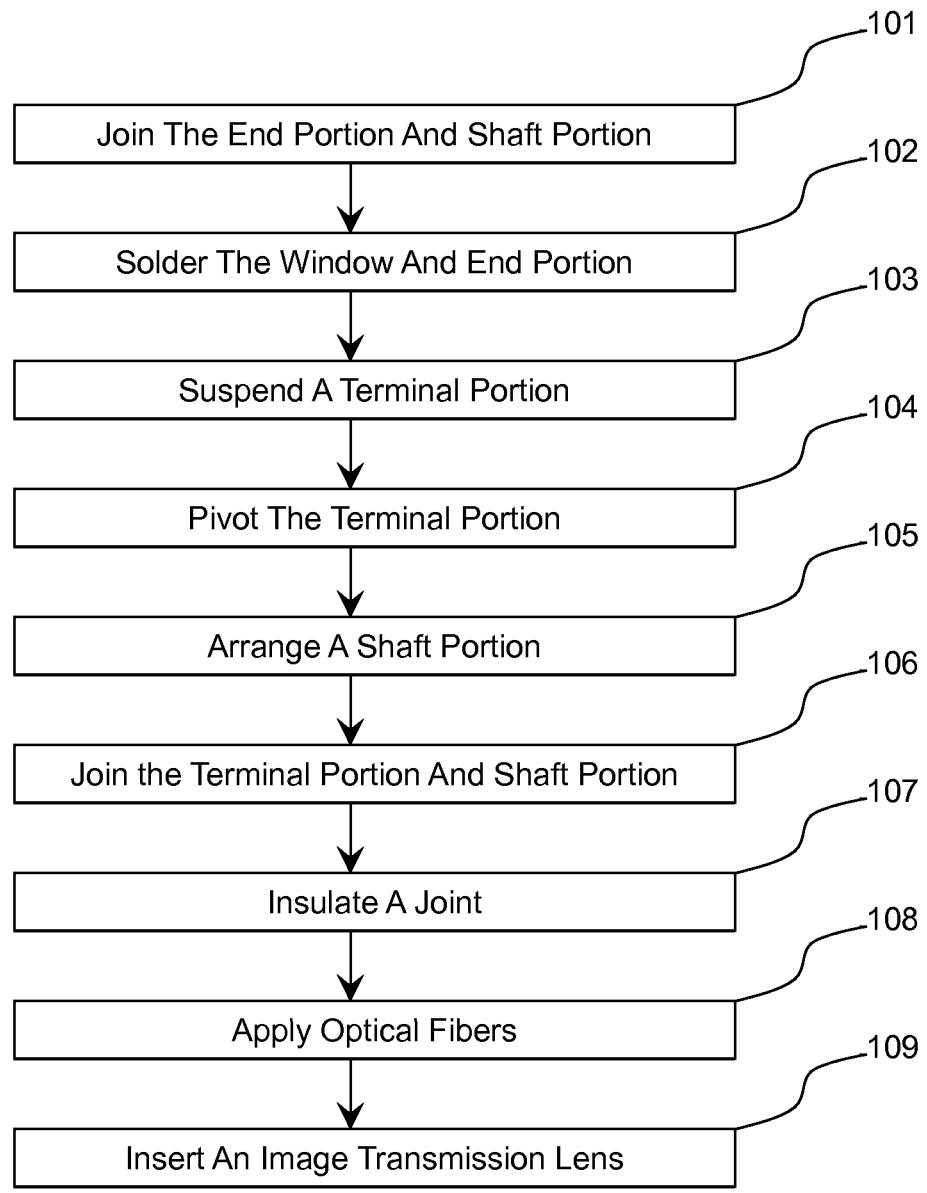
FIG. 5 is a schematic flow diagram of a process to manufacture an endoscope.

FIG. 5 shows a schematic flow diagram of a process to manufacture an endoscope. Although it is also possible with the process to produce endoscopes that differ from those presented above with reference to FIGS. 1 through 4, hereafter reference numbers from FIGS. 1 through 4 are used by way of example for the sake of clarity.

In a first step 101, an end portion 54 and a shaft portion 52 of an interior body 50 are joined, for instance by soldering or welding. The end portion 54 comprises a hollow space that leads into a lumen of the shaft portion 52 on the proximal end of the end portion 54 after joining. On the opposite, distal end of the end portion 54, this portion comprises an opening to the hollow space.

In a second step 102, a window 60 is welded or otherwise joined into or onto the aforementioned opening of the end portion 54. After that, the window 60 hermetically closes the opening in the end portion 54. In particular, the joining connection between the window 60 and the end portion 54 is of such a nature that no water vapor can penetrate inside the interior body 50 upon autoclaving, even at customary autoclaving temperatures of 140 degrees C. or more and at customary autoclaving pressures of several bar. To avoid or at least to minimize mechanical tensions resulting from different thermal expansion of the window 60 and of the end portion 54, the materials for the window 60 and end portion 54 are selected in such a way that their linear heat expansion coefficients are as similar as possible.

In a third step 103, a terminal portion 44 is suspended in an overlapping section 55, 56 on the end portion 54. In a fourth step 104, the terminal portion 44 is pivoted around an axis on or close to the overlapping section and is moved into the foreseen position. Instead of this suspending 103 and pivoting 104, the terminal portion 44 can be placed on the end portion 54 of the interior body 50, for instance through a linear motion, which at least at the end is not parallel to the axis of the endoscope 10.

In a fifth step 105, a shaft portion 42 is positioned bordering on the terminal portion 44. For this purpose, the shaft portion 42 is pushed into place over the interior body 50, in particular in the axial direction of the endoscope 10. In a sixth step 106, the terminal portion 44 and shaft portion 42 are joined, for instance by welding or soldering.

In a seventh step 107, a joint is insulated between a border of the window 60 and a border of a corresponding opening of the terminal portion 44, for instance by means of an O-ring made of an elastomer and/or by cement, silicon, resin, or another polymer. The seventh step 107 can, alternatively, be executed together with the third step or before the fifth step 105 or before the sixth step 106.

In an eighth step 108, optical fibers are applied from the proximal end 30 to the light outlet openings 46 on the distal end 20 of the endoscope 10. In a ninth step 109, an image transmission lens, for instance a rod lens system according to Hopkins, is inserted into the interior body 50 of the endoscope 10. The eighth step 108 and ninth step 109 can be executed in reverse sequence. In addition, both the eighth step 108 and the ninth step 109 can be performed at an earlier stage, in particular before the third step 103.

The third step 103, fourth step 104, or the described alternatives to both these steps, as well as the fifth step 105 and sixth step 106, can be executed as a self-sufficient process, independently of the first step 101, second step 102, seventh step 107, eighth step 108, and ninth step 109.

The invention claimed is:

1. An endoscope having:
    a window on a distal end of the endoscope;
    a shaft-like interior body with a first material on the distal end, which said shaft-like interior body forms no external surface of the endoscope, said shaft-like interior body enclosing at least one of optical or imaging components of the endoscope;
    a mantle with a second material on the distal end;
    such that the window is mounted to the shaft-like interior body forming a hermetic seam directly between the window and the shaft-like interior body, and a cementing seam or insulation is disposed between a border of the window and the mantle;
    wherein a difference in thermal expansion coefficients of the first material of the shaft-like interior body and of a material of the window is smaller than a difference in thermal expansion coefficients of the second material of the mantle and of the material of the window to maintain the shaft-like interior body in a hermetic insulated state.

2. The endoscope according to claim 1, wherein the window hermetically closes an opening on the shaft-like interior body.

3. The endoscope according to claim 1, wherein the window and the shaft-like interior body are welded together.

4. The endoscope according to claim 1, wherein the first material is a melting alloy.

5. The endoscope according to claim 1, wherein the window is of sapphire or another corundum.

6. The endoscope according to claim 1, wherein the mantle includes a terminal portion on the distal end and a shaft portion, the terminal portion and the shaft portion are joined.

7. The endoscope according to claim 1, and moreover with a plurality of light outlet openings on both opposite sides of the window, such that the light outlet openings on one side of the window are positioned offset from the light outlet openings on the other side of the window.

8. A process to manufacture an endoscope with the following steps:
    attach a window onto a distal end of a shaft-like interior body, the shaft-like interior body being formed from a first material and enclosing at least one of optical or imaging components of the endoscope;
    surround the shaft-like interior body with a mantle, the mantle being formed from a second material; and
    insulate a joint between the window and a mantle of the endoscope;
    wherein a difference in thermal expansion coefficients of the first material and of a material of the window is smaller than a difference in thermal expansion coefficients of the second material and of the material of the window.

9. The process according to claim 8, with the following step:
    join a terminal portion and a shaft portion of the mantle.

10. The process according to claim 8 with the following steps, which are executed after soldering and before insulating:
    suspend the terminal portion on an overlapping section on a distal end of the shaft-like interior body;
    pivot the terminal portion around an axis close to the overlapping section.

11. The process according to claim 8 with the following step:
    suspend the terminal portion after inserting the light conductor in the light outlet openings of the terminal portion.

* * * * *